(12) United States Patent
Zardi et al.

(10) Patent No.: US 8,367,867 B2
(45) Date of Patent: Feb. 5, 2013

(54) PROCESS AND PLANT FOR UREA PRODUCTION

(75) Inventors: Federico Zardi, Breganzona (CH); Sergio Debernardi, Carabbia (CH)

(73) Assignee: Urea Casale S.A. (CH)

( * ) Notice: Subject to any disclaimer, the term of this patent is extended or adjusted under 35 U.S.C. 154(b) by 20 days.

(21) Appl. No.: 12/679,827

(22) PCT Filed: Oct. 4, 2007

(86) PCT No.: PCT/EP2007/008611
§ 371 (c)(1),
(2), (4) Date: Apr. 28, 2010

(87) PCT Pub. No.: WO2009/043365
PCT Pub. Date: Apr. 9, 2009

(65) Prior Publication Data
US 2010/0210874 A1    Aug. 19, 2010

(51) Int. Cl.
*C07C 273/04* (2006.01)

(52) U.S. Cl. ............................ 564/67; 564/70; 564/72
(58) Field of Classification Search .................... 564/67, 564/70, 72
See application file for complete search history.

(56) References Cited

U.S. PATENT DOCUMENTS

| 2,087,325 A | 7/1937 | Lawrence et al. |
| 2004/0152918 A1 | 8/2004 | Filippi et al. |

OTHER PUBLICATIONS

V.I. Kucheryavy et al., "Application of Urea Synthesis", 1970, pp. 42-43 and 226-229.
D.M. Gorlovsky et al., "Urea Technology", 1981, pp. 151-179.

*Primary Examiner* — Peter G O Sullivan
(74) *Attorney, Agent, or Firm* — Akerman Senterfitt (57) ABSTRACT

A process for producing urea is disclosed, wherein liquid ammonia and carbon dioxide are reacted in a high-pressure synthesis section (100), and at least part of the carbon dioxide is fed to said synthesis section (100) in liquid phase. A plant operating according to said process and a method for modernizing existing plants accordingly are also disclosed.

13 Claims, 7 Drawing Sheets

PROCESS AND PLANT FOR UREA PRODUCTION

FIELD OF APPLICATION

The present invention relates to a process and plant for urea production. The invention also relates to a method for modernization of an existing plant for urea production.

PRIOR ART

According to known art, urea is produced by reacting liquid ammonia and gaseous carbon dioxide ($CO_2$) in a high-pressure reactor, typically a vertical, stainless-steel vessel containing a series of trays to improve the mixing of the reactants. Ammonium carbamate is formed in the liquid phase of the high-pressure reactor as intermediate product, and urea is produced, also in liquid phase, by dehydratation of said ammonium carbamate. The product exiting the reactor is substantially an aqueous solution comprising urea, carbamate and free ammonia.

In more general terms, a urea plant comprises a synthesis section and a recovery section. The recovery section receives a liquid mixture of urea, carbamate, ammonia and water from the synthesis section, and provides an aqueous solution of recycled carbamate and ammonia to the synthesis section. A urea finishing or purifying section can also be provided downstream the recovery section.

Most of the current plants for producing urea use the so-called stripping process, which is aimed to recover most of the carbamate contained in said aqueous solution leaving the high-pressure (HP) reactor, in a so called high-pressure loop (i.e. at a pressure substantially equal to working pressure of the reactor), increasing in this way the energy efficiency.

Stripping processes are known since decades and substantially include the carbon dioxide ($CO_2$) stripping process and ammonia stripping (or self-stripping) process. To carry out a stripping process, the HP synthesis section comprises at least a reactor, a stripper and a condenser.

In a $CO_2$-stripping process, the ammonium carbamate is stripped from the urea solution with the aid of the fresh carbon dioxide feed. Stripping takes place typically in a vertical, steam-heated tubular heat exchanger, wherein unconverted carbamate dissociates into gaseous ammonia and carbon dioxide, which are then recombined in a condenser obtaining liquid carbamate. Said liquid carbamate is recycled to the reactor. The condensation heat is also used to produce low-pressure steam which is used in downstream purification section, thus minimizing the energy consumption.

In a self-stripping process, the stripping effect is given by gaseous ammonia generated from thermal dissociation of the carbamate solution produced in the reactor; hence no stripping agent is required and the gaseous carbon dioxide feed is normally introduced directly into the reactor.

Figure 7:
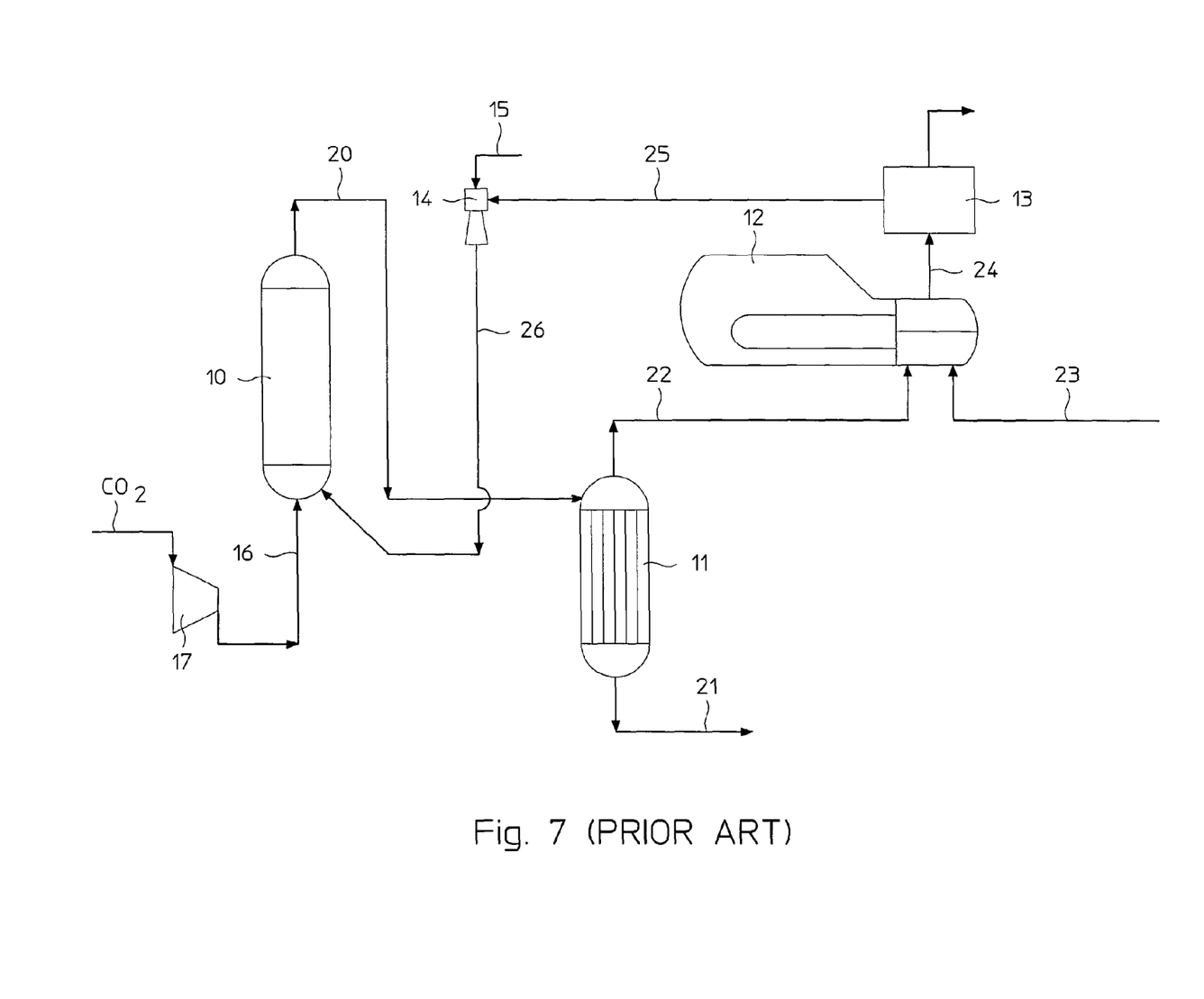
FIG. 7 is a simplified scheme of the high-pressure loop of a known ammonia-stripping (or self-stripping) process.

A simplified scheme of the high-pressure loop of a known ammonia-stripping (or self-stripping) process is shown in FIG. 7.

The HP loop essentially comprises a reactor 10, a stripper 11, and shell-and-tube condenser 12. The urea synthesis reaction takes place inside the reactor 10, producing a liquid mixture of urea, carbamate and ammonia, which is fed to the stripper 11 via duct 20. Said stripper 11 is, for example, a vertical, steam-heated tube heat exchanger with said liquid mixture flowing inside tubes.

The liquid phase obtained in stripper 11 is fed to a recovery/purifying section (not shown) via duct 21; while vapors exiting the stripper are sent to the condenser 12 via a duct 22. Recycled carbamate coming from the recovery section is also fed to the condenser 12, through duct 23, and the liquid formed in said condenser 12, containing recycle carbamate, is sent to reactor 10.

More in detail, the liquid produced in condenser 12, which contains a certain amount of inert gases, is sent to a separator 13 for removing said inerts, and the liquid phase is fed to an ejector 14, via ducts 24 and 25 respectively. Said ejector 14 is powered by the fresh ammonia feed of line 15, so that fresh ammonia and recycled carbamate are sent to the reactor 10 via duct 26.

The carbon dioxide is fed to reactor 10 by flow line 16, with the help of a multi-stage compressor 17 adapted to raise the carbon dioxide pressure up to the operating pressure of the synthesis loop (over 100 bars).

Summarizing, a liquid ammonia input is provided to reactor 10 is through said ejector 14 and line 26, while a gaseous $CO_2$ input is provided to the same reactor 10 through line 16 and the compressor 17.

In a $CO_2$-stripping plant, gaseous carbon dioxide is fed to the stripper instead of reactor, via a multi-stage compressor. $CO_2$ acts as a stripping agent, which causes decomposition of the carbamate and partial separation of the free ammonia. Gaseous phase exiting the stripper is sent to a condenser, which produces an aqueous solution and a vapour stream, including the recycled carbamate as well as the ammonia and carbon dioxide feed, which are sent to reactor.

The above described plant configurations are open to many modifications, but according to known art the carbon dioxide is always fed in gaseous state to the stripper or the reactor of the synthesis section. In other words, the prior-art teaches to provide a gaseous carbon dioxide feed to the synthesis section, i.e. to the stripper of a $CO_2$-stripping plant or into the reactor itself of a self-stripping plant.

SUMMARY OF THE INVENTION

The problem underlying the invention is to improve the energy efficiency of known process and plant for urea production. Energy efficiency, in fact, is penalized by the various components and/or auxiliaries requiring energy, and inter alia by the multi-stage compressor of the gaseous $CO_2$.

The basic idea underlying the invention is that at least part of the carbon dioxide is fed to the synthesis section in liquid phase.

Hence, the above stated problem is solved with a process for producing urea wherein liquid ammonia and carbon dioxide are fed to a synthesis section and reacted into said section to form urea, characterized in that at least part of the carbon dioxide is fed to said synthesis section in liquid phase.

According to a first embodiment of the invention, a part of carbon dioxide feeding to the synthesis section is in liquid phase and the remaining part of said carbon dioxide feeding is gaseous.

According to a second embodiment of the invention, the full carbon dioxide input to the synthesis section is in liquid phase, and no input of gaseous $CO_2$ is provided to the synthesis section. This second embodiment is applicable to a self-stripping process, wherein no gaseous $CO_2$ is required for stripping.

The synthesis section of a urea plant generally comprises at least a reactor, a stripper and a condenser forming a high-pressure loop. According to embodiments of the invention, a liquid $CO_2$ is fed to the reactor and/or to the condenser of said high-pressure loop of the synthesis section. Feeding liquid CO2 to the reactor and/or to the condenser is preferred because said components, during operation, already contain liquid.

More in detail, according to an embodiment of the invention, the full liquid amount of CO2 is directed to the reactor. According to another embodiment, the full liquid amount of CO2 is directed to the condenser; according to still another embodiment, the liquid amount of CO2 is partly directed to the reactor and partly directed to the condenser. In all the above embodiments, there can be a further input of gaseous CO2. In a self-stripping process, said further input of gaseous CO2 is optional and preferably directed to the reactor; in a CO2-stripping process said gaseous CO2 is required and directed to the stripper.

According to another aspect of the invention, liquid carbon dioxide input is mixed with at least part of the liquid ammonia input; the resulting mixture is then fed to the reactor and/or condenser of the synthesis section.

An object of the invention is also a plant for producing urea with the above process, said plant comprising at least:
a synthesis section;
feeding means providing an input of fresh ammonia and an input fresh of carbon dioxide to said synthesis section;
characterized by said feeding means being adapted to feed at least part of said input of carbon dioxide to said synthesis section in liquid phase.

Preferably, the feeding means comprises mixing means disposed to mix at least part of the liquid ammonia with the liquid carbon dioxide, and feed the so obtained liquid mixture to the appropriate component of the synthesis section.

In a preferred embodiment, said mixing means comprise a so-called T-mixer or a nozzle; preferably said nozzle has a portion with separate coaxial ducts for liquid carbon dioxide and liquid ammonia, and a second portion acting as a mixing zone for said liquid carbon dioxide and ammonia. More in detail, the mixer has an internal duct with a convergent outlet substantially corresponding to a convergent portion of the external duct, thus obtaining a mixing zone with decreasing cross section in the axial direction. Said mixing zone of the nozzle is followed by a constant cross-section portion and a divergent portion, to slow down the liquid.

Another object of the invention is a method for improving efficiency of an existing plant for producing urea, said method being characterized by providing further means adapted to feed at least part of the carbon dioxide input to the synthesis section in liquid phase.

According to one embodiment of the above method, a CO2-stripping unit is revamped maintaining the existing gaseous CO2 feeding means to the stripper, and providing further liquid carbon dioxide feeding means directed to the reactor and/or to the condenser of the HP loop.

In another embodiment, a self-stripping unit is revamped replacing the existing gaseous CO2 feeding means with the inventive liquid CO2 feeding means. These lasts can be directed o the reactor and/or to the condenser of the HP loop.

Preferably, the liquid carbon dioxide feeding means used in said method for improving efficiency of an existing urea plant comprise a mixer as defined above. According to equivalent aspects of the invention, the new feeding means are provided to feed the liquid carbon dioxide to the reactor and/or to the condenser of the synthesis section.

In all above embodiments, suitable means to liquefy and pump the carbon dioxide can be provided, according to per se known art.

It should also be noted that reaction, stripping and condensation can be equally carried out in a single unit or more unit in parallel, according to the needs.

The invention has many advantages over the prior art.

It has been found that feeding the synthesis section with at least part of the carbon dioxide in liquid state yields a surprising improvement in the energy efficiency of the process.

It should be noted that the urea forming reaction takes place in the liquid phase containing carbamate. In prior art processes and plants, liquid ammonia and gaseous CO2 entering the reactor, namely the reaction zone inside the reactor, are mixed with the objective to create an intimate contact between the two phases (that is liquid and gas) and favor the mass and heat exchange between said reactants. However, yield of reaction is limited by the rate of mass transfer from the gas phase to the liquid phase, wherein reaction actually takes place.

The invention overcomes this limitation by providing both reactants ammonia and CO2 in a liquid phase, the yield being no longer limited by the gas-to-liquid mass transfer. In other words, the reactants are mixed in a more effective manner inside the reaction zone, with advantages also in terms of the reaction yield.

It should also be noted that energy consumption of the multistage compressor of the carbon dioxide (which is indispensable in the prior art) is reduced or even avoided, as pumping a liquid CO2 requires less energy than compression of a gaseous CO2. In a CO2-stripping plant the amount of gaseous CO2 to be compressed is reduced, as part of the CO2 is fed in a liquid state; in a self-stripping unit the compressor is no longer necessary and the full CO2 input can be pumped in liquid form to the synthesis section. Reduced energy consumption compensates for additional energy and equipment required for liquefying and pumping the CO2.

Further features and advantages of the present invention will appear more clearly from the following non-limiting description of embodiments thereof, made with reference to the attached drawings.

DETAILED DESCRIPTION OF THE DRAWINGS

Figure 1:
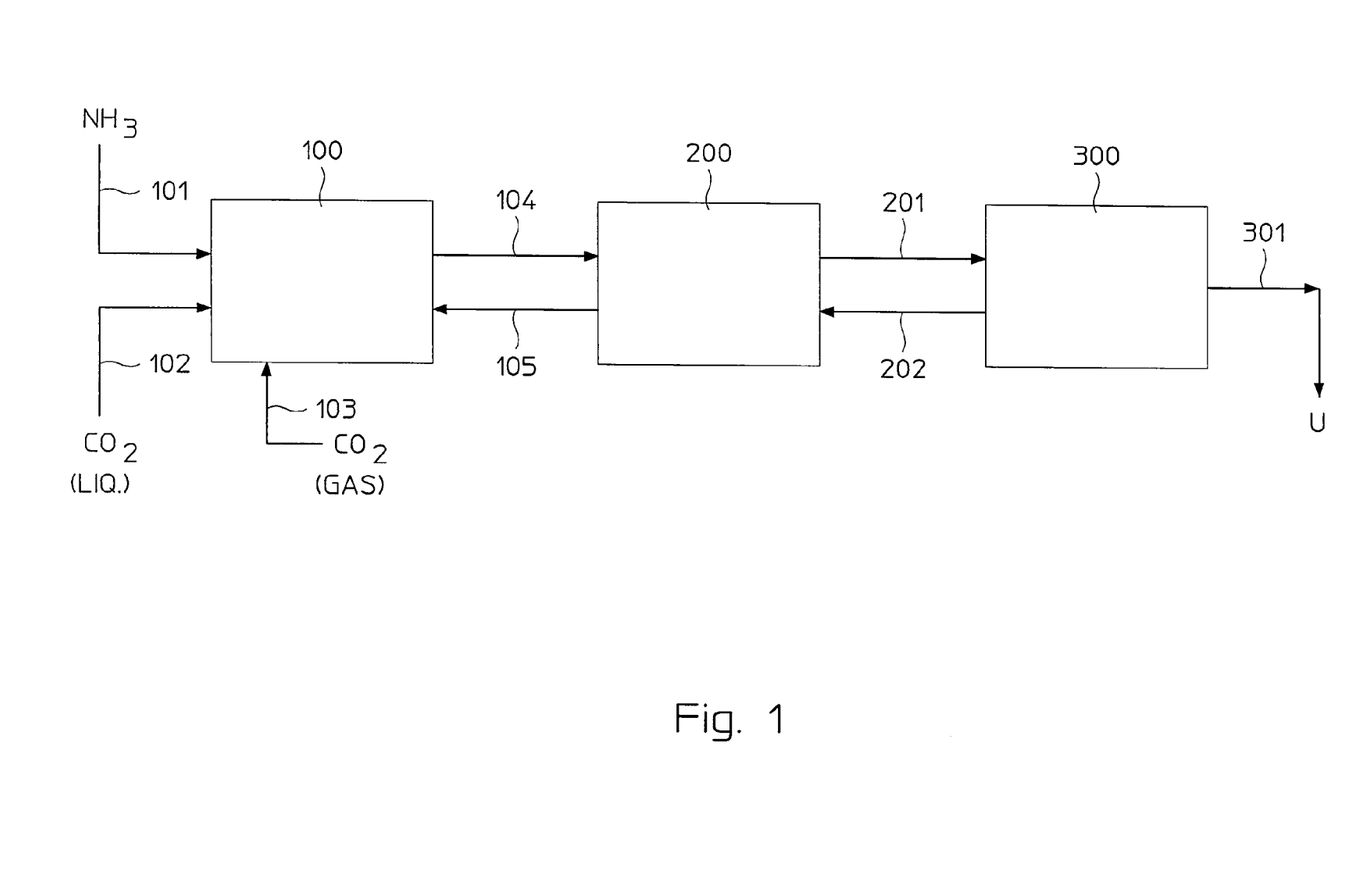
FIG. 1 is a general block scheme of a urea plant according to the invention.

Referring to FIG. 1, a urea plant comprises a synthesis section 100 operating at high pressure, a recovery section 200 and optionally a finishing section 300. FIG. 1 refers in the most general way to a urea plant, such as self-stripping, CO2 stripping or other.

Synthesis section 100 is fed through input line 101 with fresh liquid ammonia and is also fed through line 102 with fresh liquid carbon dioxide. Another input line 103 of gaseous CO2 can be provided if necessary, e.g. if the plant operates according to a CO2-stripping process and section 100 comprises a stripper which receives an input of gaseous carbon dioxide.

Line 102 is connected to suitable means for obtaining liquid carbon dioxide, which are per se known and thus not described in detail.

Ammonia and carbon dioxide are the reactants of the urea producing reaction, which is carried out in said synthesis section 100. An aqueous solution comprising urea, carbamate and unreacted ammonia is obtained in synthesis section 100 and fed to recovery section 200 via line 104; said section 200 obtains a solution comprising recycled carbamate and ammonia, which is recycled via line 105 to the synthesis section.

Said recovery section 200 is connected via flow lines 201, 202 to the finishing section 300, wherein urea is produced and a solution of carbamate and ammonia is sent back to the recovery section. Purified urea U is discharged through line 301.

Sections 200 and 300 are conventional and are not essential for the invention, and will not be described in detail.

Figure 2:
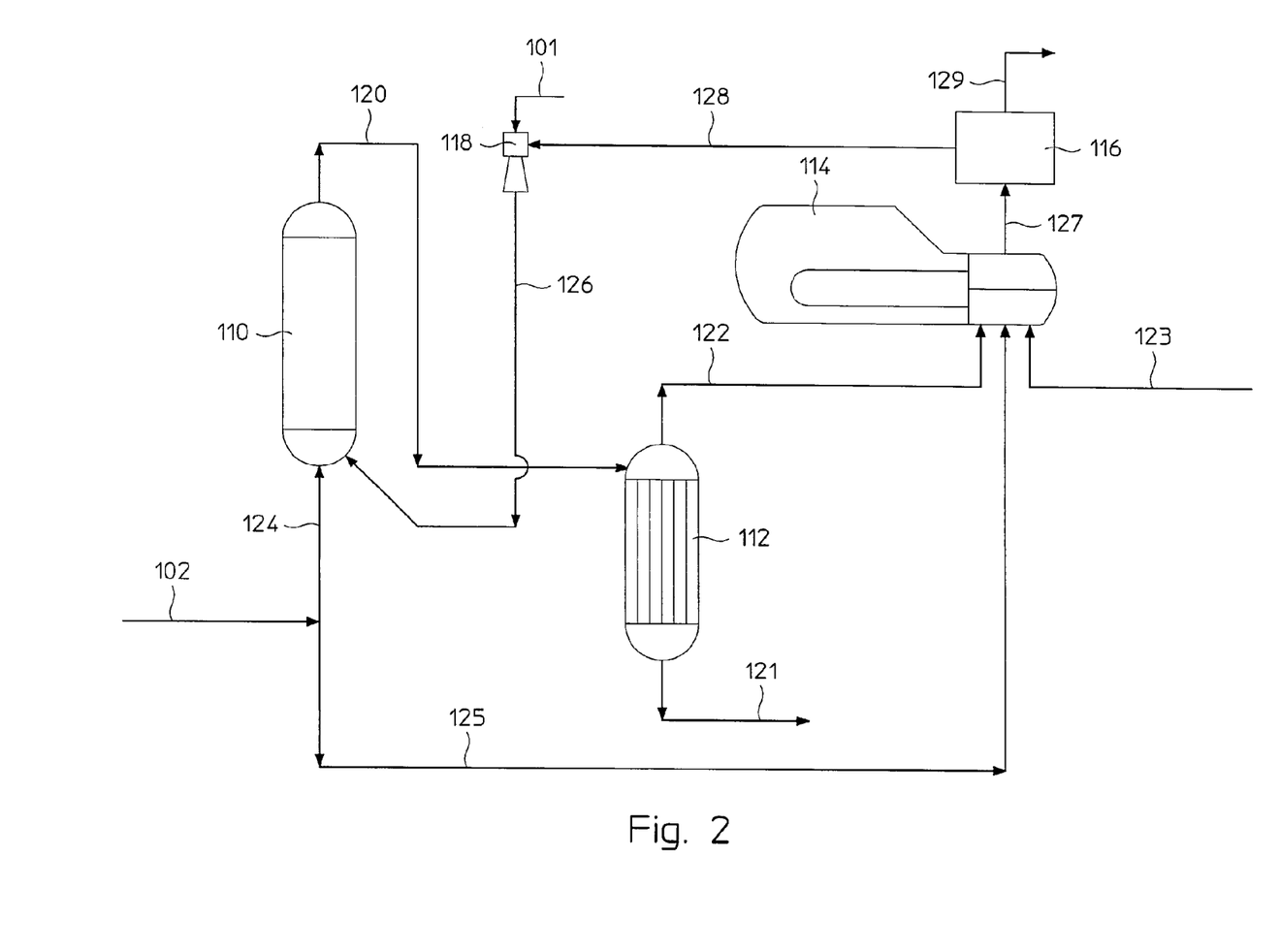
FIGS. 2 and 3 are simplified schemes of the high-pressure loop of a self-stripping plant for producing urea, according to embodiments of the invention.

Referring to FIG. 2, the main components of synthesis section 100 of a self-stripping plant, according to one embodiment of the invention, are shown.

The HP loop comprises essentially a reactor 110, a stripper 112 and a condenser 114. Stripper 112 is for example a vertical, steam-heated shell-and-tube heat exchanger, while condenser 114 is a horizontal shell-and-tube heat exchanger.

A solution substantially comprising urea, carbamate and unreacted ammonia is produced in the reactor 110 and is sent from top of said reactor 110 to the stripper 112, via a flow line (or duct) 120.

Liquid phase exiting the stripper 112, comprising carbamate and urea, is sent via flow line 121 to a recovery/finishing section, not shown. Gaseous phase from stripper 112 is sent to the condenser 114, through line 122. Recycle carbamate coming from the recovery section is also fed to the condenser 114, via line 123.

The output of condenser 114 is a liquid mixture, apart from a few inerts, which is sent to a carbamate separator 116 (flow line 127) and recycled to reactor 110 by means of an ejector 118 powered by the liquid ammonia feed. Inerts are vented from separator 116 through line 129, and the liquid phase is sent to ejector 118 via flow line 128, said ejector also receiving the fresh ammonia from line 101. A flow substantially comprising fresh ammonia and recycled carbamate is then fed to reactor 110 via line 126.

A liquid carbon dioxide is fed to reactor 110, from input line 102 and via line 124. A further flow line 125 provides liquid CO2 input to the condenser 114, which is mixed in the tube-side of the condenser with the gaseous phase coming from the stripper and the recycle carbamate. Hence, liquid CO2 is fed partly to the reactor 110 via line 124, and partly to the condenser 114 via line 125 in parallel to line 124.

In other embodiments (not shown) the full amount of liquid CO2 is fed either to the reactor 110 or to the condenser 114.

A further input of CO2, but in a gaseous phase, can also be provided to reactor 110. In self-stripping units, however, it is preferred to feed all the carbon dioxide in the liquid phase, to the reactor and/or the condenser as shown in FIG. 2.

Figure 3:
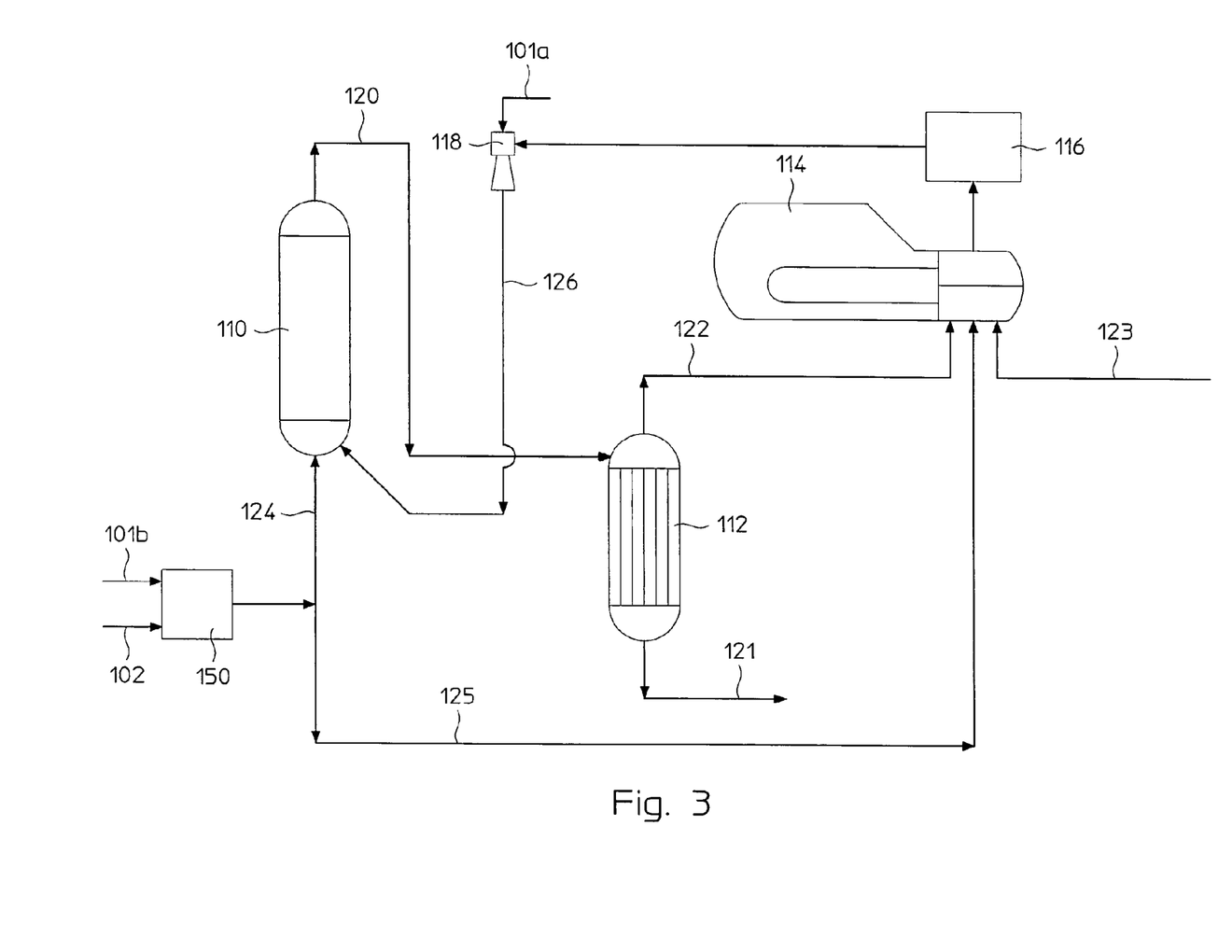

According to a variant shown in FIG. 3, a part of the liquid ammonia is fed with flow line 101a to power the ejector 118, and a part of the liquid ammonia is fed via flow line 101b to a mixer 150, wherein said liquid ammonia and liquid carbon dioxide from line 102 are mixed, and the resulting liquid mixture is sent to reactor 110 and condenser 114 via flow lines 124 and 125. As above, further embodiments of the invention provides that the mixture produced in the mixer 150 is fed to either the reactor 110 or the condenser 114 alone; a further input of gaseous CO2 can also be provided to the reactor 110.

Figure 4:
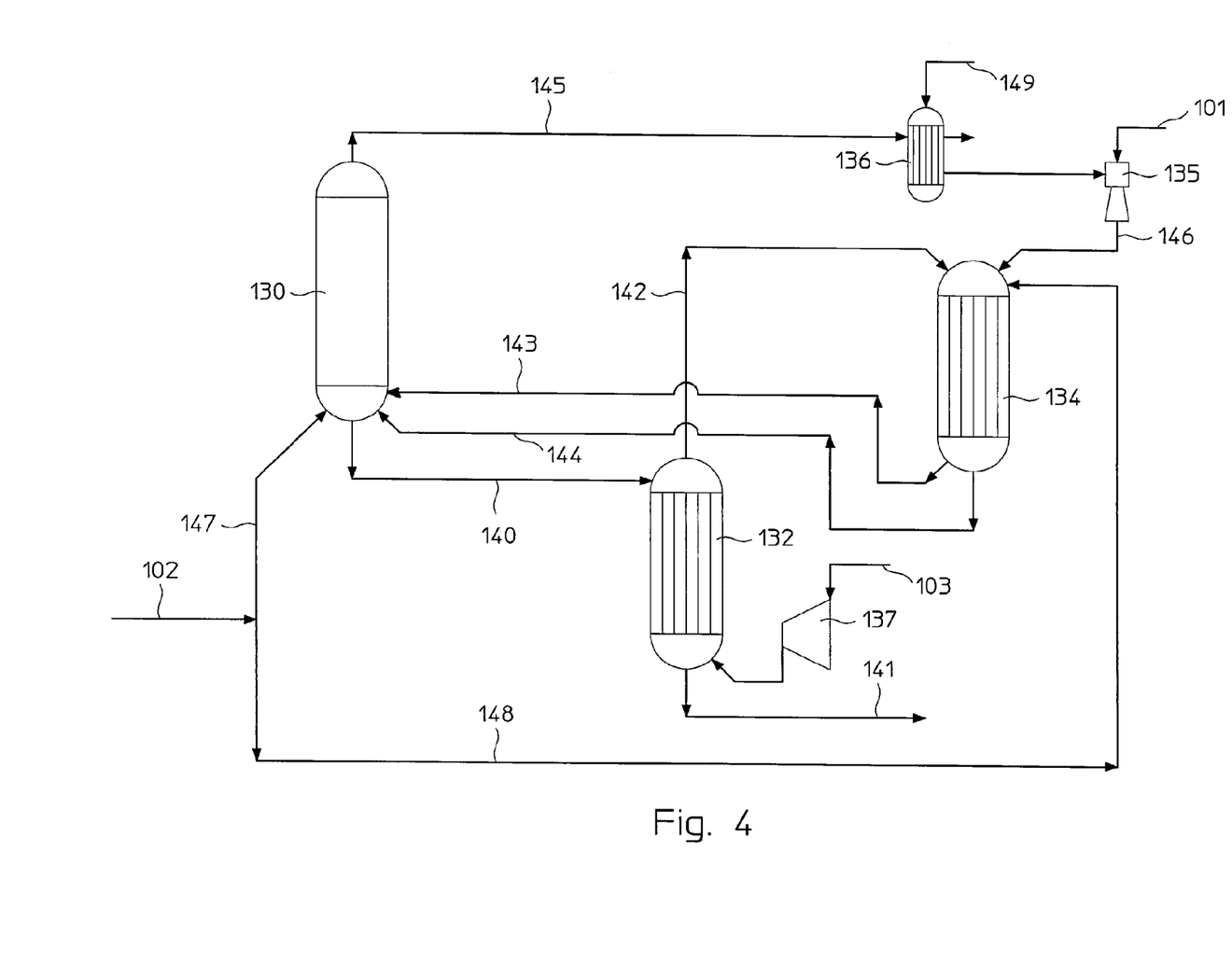
FIGS. 4 and 5 are simplified schemes of the high-pressure loop of a CO2-stripping plant for producing urea, according to embodiments of the invention.

Turning to FIG. 4, an application to a CO2-stripping unit is shown. The HP loop comprises a reactor 130, a stripper 132 and a shell-and-tube condenser 134.

A solution comprising urea, carbamate and ammonia is produced in the reactor 130 and is sent to the stripper 132, via a duct 140. Said stripper 132 is fed with gaseous CO2, which is the stripping agent, by flow line 103 and compressor 137.

Gaseous CO2 acts as a stripping agent, to promote decomposition of the ammonium carbamate. Liquid phase from stripper 132, including a partially purified urea solution, is sent to a recovery/finishing section via flow line 141, while gaseous phase is sent to the condenser 134 via line 142.

Gas from top of reactor 130 are sent to a scrubber 136, via line 145; said gas are subjected into said scrubber 136 to absorption with diluite recycle carbamate solution coming from recovery section via duct 149.

Liquid phase from scrubber 136 is sent to an ejector 135, powered by liquid ammonia entering from line 101; the flow exiting said ejector 135, containing the fresh ammonia feed and recycled carbamate, is directed to condenser 134 via flow line 146.

Liquid and gaseous phase from condenser 134 are separately conveyed to reactor 130 via flow lines 143 (gas) and 144 (liquid).

According to embodiments of the invention, liquid carbon dioxide is fed to either the reactor 130, the condenser 134, or both. FIG. 4 shows an embodiment wherein flow lines 147 and 148 feed part of the liquid CO2 to the reactor 130, and part of the liquid CO2 to the condenser 134 respectively.

Figure 5:
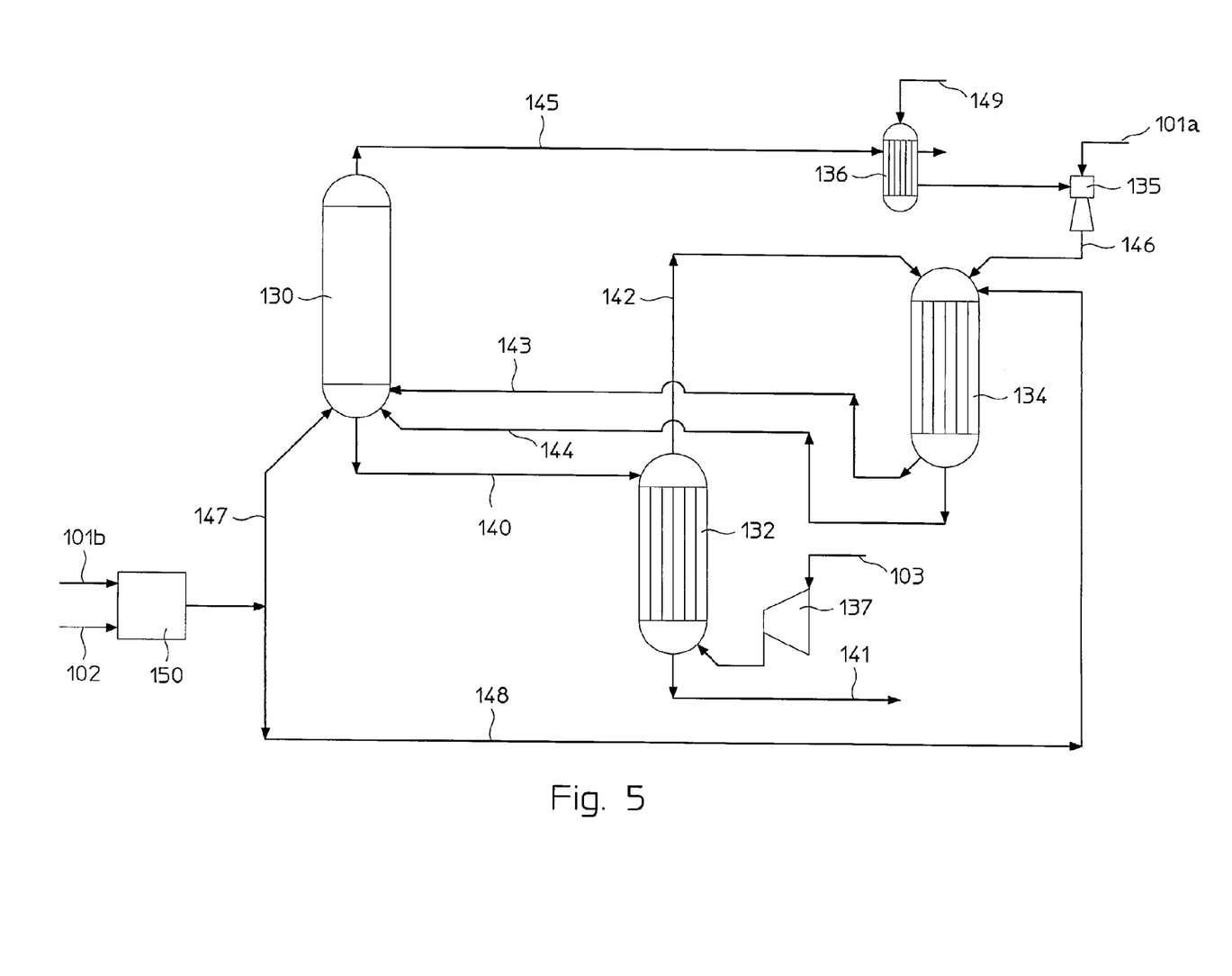

Referring to the variant of FIG. 5, a mixer 150 is provided on the liquid CO2 feed line, and liquid ammonia is fed to ejector 135 and to said mixer 150 via flow lines 101a and 101b. Hence, a part of the liquid ammonia feed is used to power the ejector, and a part is mixed with the liquid carbon dioxide. The ammonia/carbon dioxide mixture produced in said mixer 150 is sent to either the reactor, the condenser or both.

It should be noted that FIGS. 2 to 5 are simplified schemes and details and auxiliaries (e.g. pumps, valves, etc.), which are well known to the skilled person, are not shown. It should also be noted that said schemes are open to many variants, also well known in the art.

Figure 6:
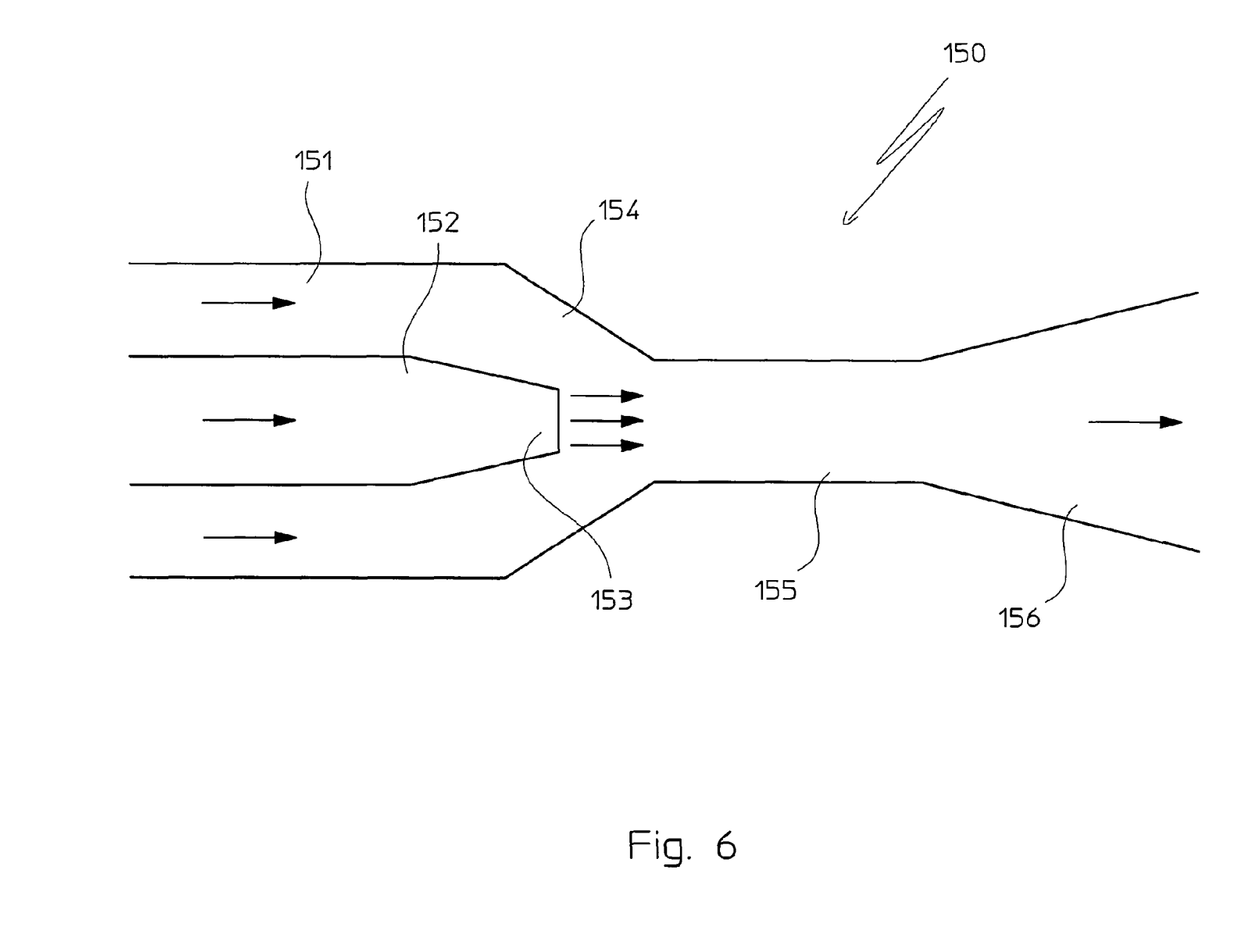
FIG. 6 is a simplified cross section of a nozzle for feeding a mixed flow of liquid ammonia and carbon dioxide, according to a preferred aspect of the invention.

Referring to FIG. 6, in a preferred embodiment the mixer 150 is a nozzle comprising an external duct 151 for liquid ammonia and an internal, coaxial duct 152 for liquid CO2. Liquid ammonia flows in the annular space around duct 152 and is intimately mixed with liquid CO2 exiting the duct 152. Said duct 152 has an outlet convergent portion 153, corresponding to a convergent portion 154 of the external duct. Said convergent portion 154, reducing the cross section of the nozzle, provides acceleration of the liquid flow and improves the mixing of liquid ammonia and CO2. A mixing portion with decreasing cross section is thus obtained between ducts 151 and 152, around and downstream the outlet 153 of the inner duct.

A following, constant cross-section portion 155 is provided for spreading the flows. Said portion 155 is followed by an outlet divergent 156 were mixed flow is slown down.

The nozzle 150 can be installed e.g. upstream the reactor 112 or condenser 116, so that the liquid ammonia/CO2 mixture is fed to said reactor or said condenser.

The invention is equally applicable to many different urea plants, including those which can be conduced to the general block diagram of FIG. 1. The invention is also applicable to modernizing of an existing urea plant, wherein liquid CO2 feeding means are provided in addition to or replacing the existing gaseous CO2 feeding means.

The invention claimed is:

1. A process for producing urea, comprising the steps of:
feeding liquid ammonia and carbon dioxide to a synthesis section comprising at least a reactor, a stripper and a condenser forming a high-pressure loop; and
reacting said liquid ammonia and carbon dioxide in said synthesis section to produce urea,
wherein at least part of said carbon dioxide is fed to said synthesis section in liquid phase.

2. The process according to claim 1, wherein a part of said carbon dioxide is fed to the synthesis section in liquid phase and the remaining part is fed to the synthesis section in gaseous phase.

3. The process according to claim 1, wherein the full carbon dioxide input to said synthesis section is in liquid state.

4. The process according to claim 1, wherein said synthesis section comprises a reactor, a stripper and a condenser, and said liquid carbon dioxide is fed either to said reactor or to said condenser.

5. The process according to claim 1, wherein said synthesis section comprises a reactor, a stripper and a condenser; a part of said liquid carbon dioxide is fed to the reactor, and a part of the liquid carbon dioxide is fed to the condenser.

6. The process according to claim 1, wherein said liquid carbon dioxide is mixed with at least part of said liquid ammonia, obtaining a liquid mixture which is fed to said synthesis section.

7. A plant for producing urea with a process according to claim 1, said plant comprising at least:
a synthesis section comprising at least a reactor, a stripper and a condenser forming a high-pressure loop; and
feeding means providing an input of fresh ammonia and an input of fresh carbon dioxide to said synthesis section;
wherein said feeding means are adapted to feed at least part of said fresh carbon dioxide input to said synthesis section in liquid phase.

8. The plant according to claim 7, further comprising mixing means disposed to mix said input of liquid carbon dioxide with at least part of said input of liquid ammonia.

9. The plant according to claim 8, wherein said mixing means comprise a nozzle comprising a first portion with separate coaxial ducts for liquid carbon dioxide and liquid ammonia, and a second mixing portion wherein liquid carbon dioxide and ammonia are mixed.

10. The plant according to claim 9, wherein said nozzle comprises an external duct and an internal, coaxial duct; the internal duct has a convergent outlet substantially corresponding to a convergent portion of the external duct, obtaining a mixing zone with decreasing cross section in the axial direction, said mixing zone of the nozzle being followed by a constant cross-section portion and a divergent to slow down the liquid mixture.

11. A method for improving efficiency of a plant for producing urea, said plant being a self-stripping or $CO_2$-stripping plant comprising at least a synthesis section comprising a reactor, a stripper and a condenser in a high-pressure loop, connected to ammonia feeding means and gaseous carbon dioxide feeding means, said method comprising providing liquid carbon dioxide feeding means connected to said synthesis section.

12. The method according to claim 11, further comprising mixing means adapted to mix an input of liquid ammonia with an input of liquid carbon dioxide and feed the resulting liquid mixture to said synthesis section.

13. The method according to claim 11, wherein liquid carbon dioxide feeding means are provided to feed liquid carbon dioxide to said reactor and/or said condenser.

* * * * *